US008663250B2

(12) United States Patent
Weber (10) Patent No.: US 8,663,250 B2
(45) Date of Patent: Mar. 4, 2014

(54) SUTURING INSTRUMENT WITH DUAL NEEDLES AND METHOD OF PASSING SUTURE

(75) Inventor: Robert M. Weber, Chino Hills, CA (US)

(73) Assignee: Arthrex, Inc., Naples, FL (US)

( * ) Notice: Subject to any disclaimer, the term of this patent is extended or adjusted under 35 U.S.C. 154(b) by 1098 days.

(21) Appl. No.: 12/198,798

(22) Filed: Aug. 26, 2008

(65) Prior Publication Data

US 2009/0062816 A1 Mar. 5, 2009

Related U.S. Application Data

(60) Provisional application No. 60/968,277, filed on Aug. 27, 2007.

(51) Int. Cl.
*A61B 17/04* (2006.01)
(52) U.S. Cl.
USPC .......................... 606/145; 606/144; 606/147
(58) Field of Classification Search
USPC .......................... 606/145, 139, 144, 147, 148
See application file for complete search history.

(56) References Cited

U.S. PATENT DOCUMENTS

| | | | | |
|---|---|---|---|---|
| 4,957,498 | A * | 9/1990 | Caspari et al. | 606/146 |
| 6,533,795 | B1 * | 3/2003 | Tran et al. | 606/144 |
| 6,770,084 | B1 * | 8/2004 | Bain et al. | 606/144 |
| 7,112,208 | B2 * | 9/2006 | Morris et al. | 606/144 |
| 7,377,926 | B2 | 5/2008 | Topper et al. | |
| 7,381,212 | B2 | 6/2008 | Topper et al. | |
| 7,585,305 | B2 * | 9/2009 | Dreyfuss | 606/144 |
| 7,879,046 | B2 * | 2/2011 | Weinert et al. | 606/139 |
| 2002/0147456 | A1 * | 10/2002 | Diduch et al. | 606/144 |
| 2003/0065337 | A1 * | 4/2003 | Topper et al. | 606/144 |
| 2003/0078599 | A1 * | 4/2003 | O'Quinn et al. | 606/144 |
| 2006/0020162 | A1 * | 1/2006 | Whayne et al. | 600/37 |
| 2008/0208221 | A1 * | 8/2008 | Murray et al. | 606/145 |

FOREIGN PATENT DOCUMENTS

EP 1 498 075 A1 1/2005
EP 1 958 574 A1 8/2008

OTHER PUBLICATIONS

"Arthrex is Reaching New Heights in Rotator Cuff Repair"; Arthrex, Inc.; 2006.
The Arthrex Scorpion; "Fulfulling the Need for Precision and Speed in Arthroscopic Rotator Cuff Repair"; Arthrex, Inc.; 2010.

\* cited by examiner

*Primary Examiner* — Melanie Tyson
*Assistant Examiner* — Todd J Scherbel
(74) *Attorney, Agent, or Firm* — Dickstein Shapiro LLP (57) ABSTRACT

An apparatus and method for passing suture in tissue repair and other surgical procedures. The apparatus includes a pair of jaws mounted on a distal end of a shaft, a handle assembly mounted on a proximal end of the shaft, and two needles mounted on the handle assembly and through a cannulation of the shaft. A dual-needle actuator communicates with the two needles. A suture is placed at the tip of the lower jaw. By advancing the dual-needle actuator relative to the body of the instrument, the two needles are pushed forward to capture the suture and advance it through the tissue to be sutured.

8 Claims, 7 Drawing Sheets

SUTURING INSTRUMENT WITH DUAL NEEDLES AND METHOD OF PASSING SUTURE

CROSS-REFERENCE TO RELATED APPLICATIONS

This application claims the benefit of U.S. Provisional Application No. 60/968,277, filed Aug. 27, 2007, the entire disclosure of which is incorporated by reference herein.

FIELD OF THE INVENTION

The present invention relates to the field of surgery and, more particularly, to a suture passing instrument with a dual-needle construct.

BACKGROUND OF THE INVENTION

Both open and endoscopic surgical procedures often require sutures to ligate, join or otherwise treat tissue. Generally, suture needles with attached suture strands are grasped either manually or by forceps and passed through the desired work site so a knot can be tied. While the procedures are fairly uncomplicated in open surgery where most suture sites are readily accessible, in endoscopic procedures, where access to the work site is not readily available, the surgeon must use auxiliary devices to be able to grasp the suture strands and pass them through desired tissue.

Although various instruments and techniques have been developed for surgical repairs requiring the passing of sutures to distant locations, instruments that allow a surgeon to quickly, accurately, and easily pass a suture through soft tissue are still needed.

BRIEF SUMMARY OF THE INVENTION

The present invention provides a suture passing instrument and surgical technique for endoscopic surgical repairs. The suture passing instrument comprises an elongated tubular member that houses two needles disposed in a side-by-side configuration. A dual-needle actuator communicates with the two needles. A suture is placed in a securing mechanism at the tip of the lower jaw. By advancing the dual-needle actuator relative to the body of the instrument, the two needles are pushed forward to capture the suture and advance it through the tissue to be sutured.

Other features and advantages of the present invention will become apparent from the following description of the invention which refers to the accompanying drawings.

DETAILED DESCRIPTION OF THE INVENTION

The present invention provides a suture passing instrument and technique for surgical repairs. The suture passing instrument comprises an elongated tubular member that houses two needles disposed in a side-by-side configuration. A dual-needle actuating structure communicates with the two needles. A handle assembly comprises a ratchet-like mechanism and a handle, the ratchet-like mechanism being pivotally connected to the handle. The ratchet-like mechanism articulates a jaw (coupled to the tip of the elongated tubular member) relative to the elongated tubular member. A suture is placed at the tip of the elongated tubular member. By actuating the ratchet-like mechanism, the jaw is articulated relative to the elongated tubular member thereby securing contact with the tissue. By actuating the handle of the handle assembly, the dual-needle actuator pushes forward the two needles to capture the suture extending within the slot and advance it through the tissue to be sutured.

Figure 9:
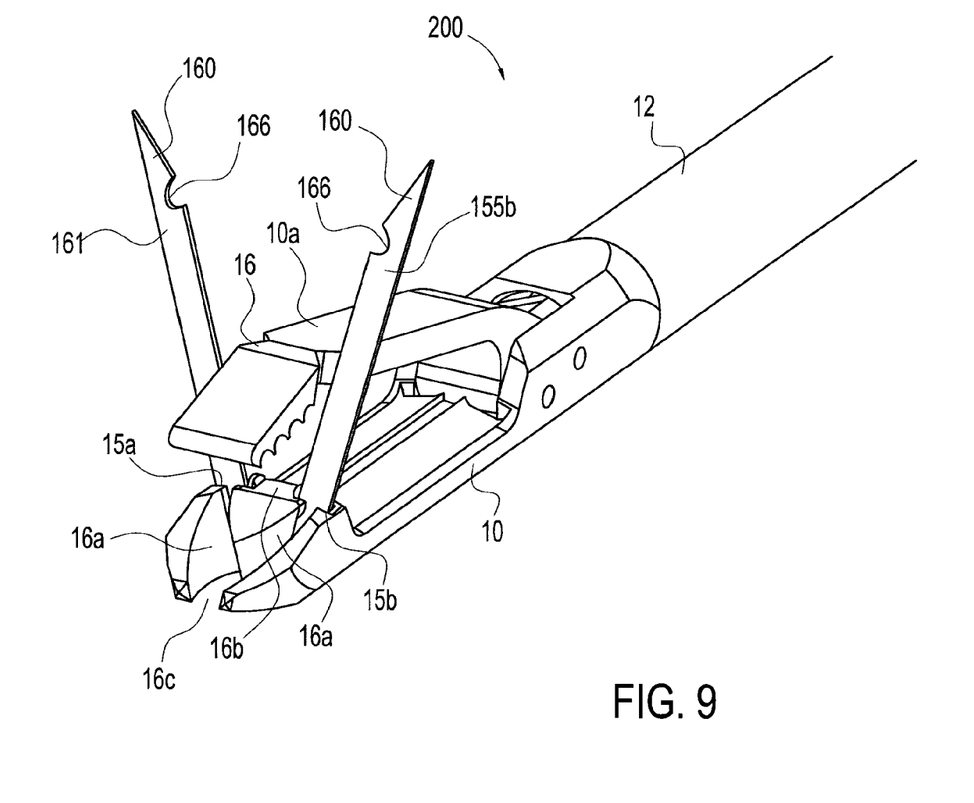
FIG. 9 illustrates an enlarged view of the distal end of a suture passing instrument according to a second embodiment of the present invention, with the two needles deployed.

Referring now to the drawings, where like elements are designated by like reference numerals, FIGS. 1-9 illustrate various structural elements of suture passing instrument 100, 200 of the present invention provided with dual needles 55a, 55b (FIG. 2) and 155a, 155b (FIG. 9).

Figure 1:
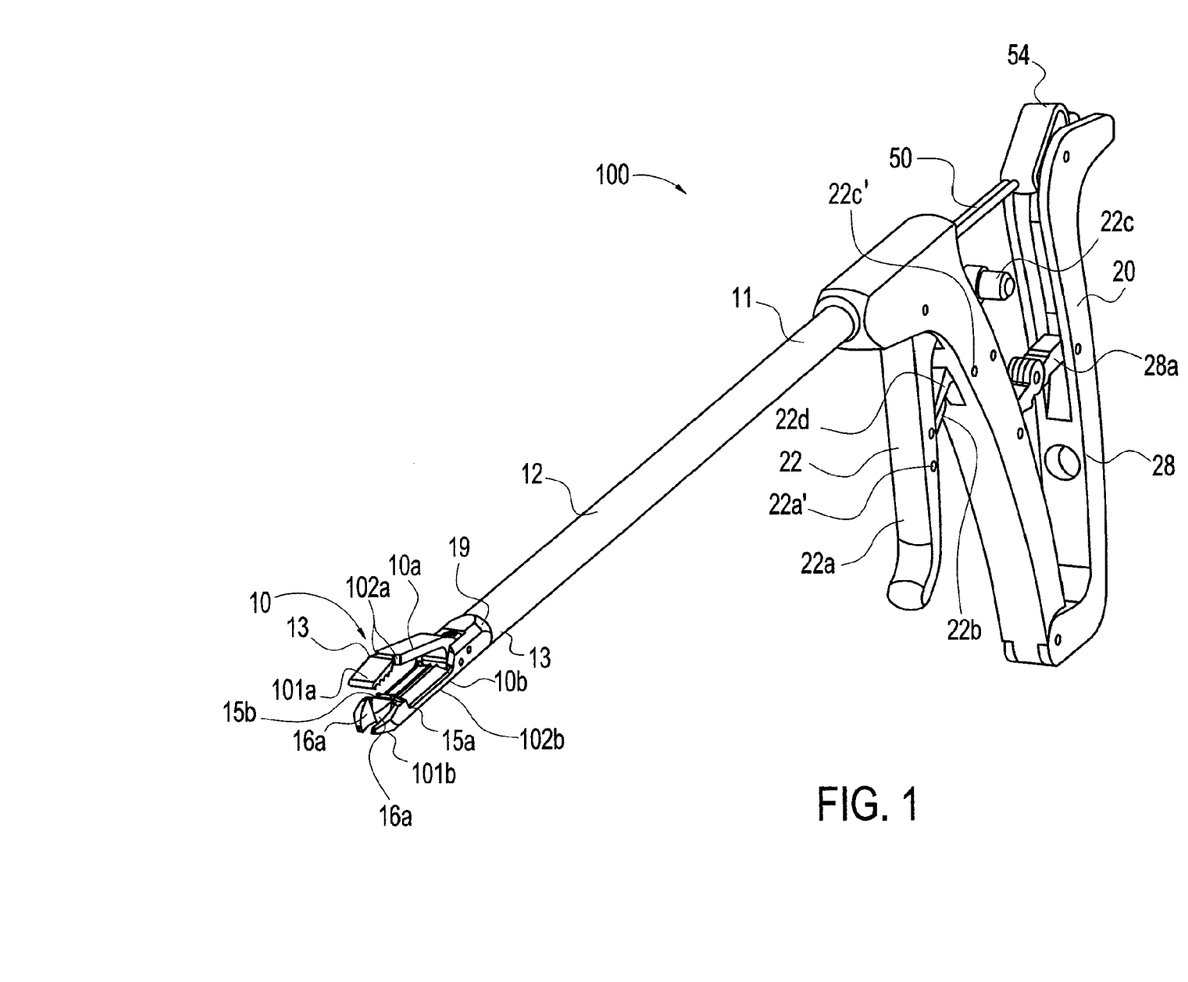
FIG. 1 illustrates a perspective view of a suture passing instrument according to a first embodiment of the present invention.

As shown in FIG. 1, suture passing instrument 100 comprises an elongated tubular member or shaft 12 having a longitudinal axis 12a, a proximal end 11, a distal end 13 and an axial throughbore therein (not shown). Elongated tubular member 12 may be a tube or a narrow-diameter rod of dimensions that permit the tubular member to be introduced through an associated cannula (for example, an 8.25 cannula) in a minimally invasive procedure, such as arthroscopic or other endoscopic procedures, or into a body cavity, such as the abdominal cavity.

Elongated tubular member 12 connects a handle assembly 20 with a tip 10 consisting of a pair of jaws 10 comprising an upper jaw 10a and a lower jaw 10b. Lower jaw 10b is provided at the distal end 13 of the instrument and is preferably integral with the tubular member 12. Upper jaw 10a (FIGS. 1 and 2) forms part of the tip 10 and may pivot with respect to the tip or lower jaw 10b. As illustrated in FIG. 1, lower jaw 10b is substantially straight with respect to the shaft, while the upper jaw 10a is provided with a first (proximal) portion 102a (which, when the jaws are in the closed position, is about parallel to the lower jaw 10b and with the longitudinal axis 12a of the device) and with a second (distal) portion 101a (which, when the jaws are in the closed position, contacts a top surface of the most distal part of the lower jaw and forms an angle of about 30 to about 60 degrees (preferably of about 45 degrees) with the longitudinal axis 12a of the device). The second (distal) portion 101a may be provided with a plurality of teeth to enhance tissue grasping and suture stability.

The lower jaw 10b of the suture passing instrument 100 includes a first (proximal) portion 102b (which is integral with the body of the instrument and is about parallel to the longitudinal axis 12a of the device) and with a second (distal)

portion 101b which has a generally pyramidal configuration (when viewed in a perspective view).

The second (distal) portion 101b may include a securing mechanism 16 which is formed integrally with the lower jaw and preferably includes two side longitudinal channels 16a (terminating in opening 16c (the end point of the tip)) and, optionally, a transversal suture loading slot 16b. The two side longitudinal channels 16a are configured to allow suture (or a strand of flexible material) to extend therethrough and to be securely positioned within two corresponding transversal slots or channels 15a, 15b (that extend at the most proximal part of the second (distal) portion 101b, and from a top surface to a lower surface of the lower jaw 10b). Slots 15a, 15b may have various configurations, for example, two lateral slots, grooves or wedges, each of the lateral slots, grooves or wedges being disposed on each end of the transversal slot, to allow increased suture positioning for future suture manipulation with the two needle construct of the invention.

When disposed in the slots 15a, 15b, the strand of suture is placed with the ends of the suture being pulled through the two longitudinal side channels 16a so that the suture reaches the two transversal slots 15a, 15b and is also placed over the transversal suture loading slot 16b of the device. When disposed in the slots 15a, 15b, the suture is securely in place for engagement by the needles 55a, 55b (FIG. 2) and 155a, 155b (FIG. 9). The suture is preferably a braided suture such as a Fiberwire™, sold by Arthrex, Inc., Naples, Fla.

Figure 2:
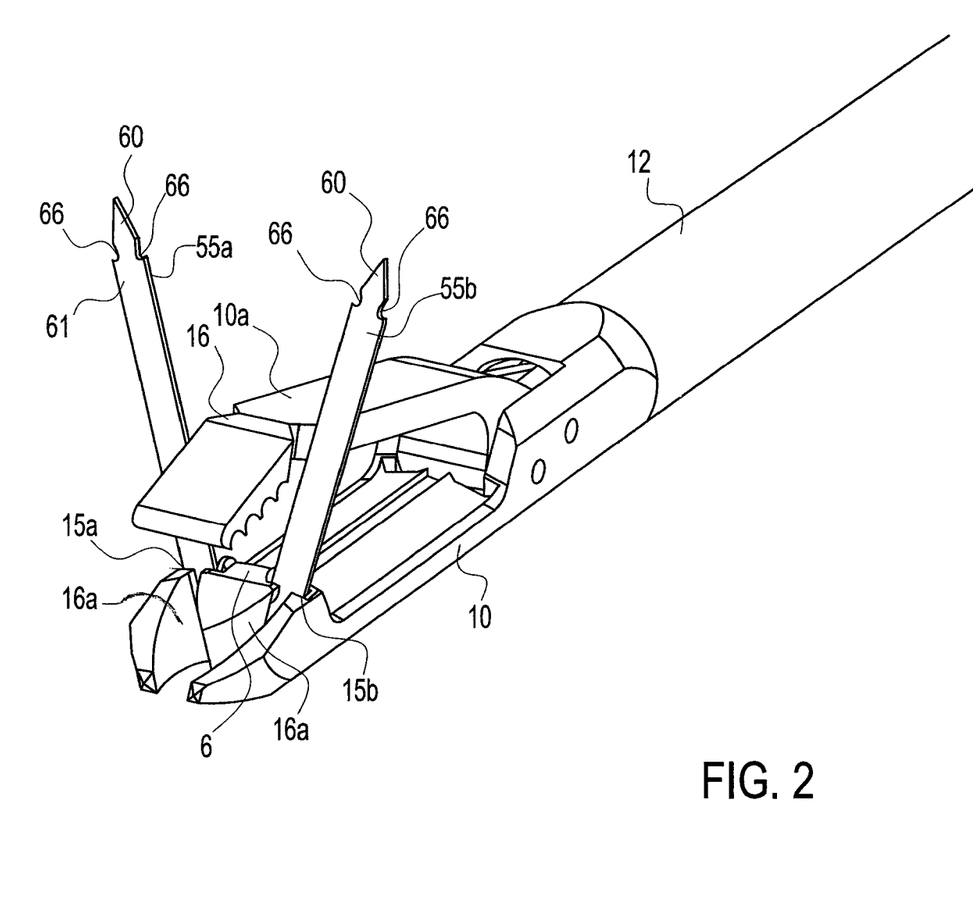
FIG. 2 illustrates an enlarged view of the distal end of the suture passing instrument of FIG. 1, with the two needles deployed.

The two slots or channels 15a, 15b are also configured to allow needles 55a, 55b, 155a, 155b to extend therethrough in the side-by-side configuration illustrated in FIGS. 2 and 9. Channels 15a, 15b are provided in a most distal end of lower jaw 10b, and, as noted, extend from a top (upper surface) of the lower jaw 10b to a bottom (lower surface) of the lower jaw 10b. Preferably, the two slots 15a, 15b have the shape of a channel with a rectangular or square cross-section to allow the two needles 55a, 55b, 155a, 155b having a generally flat configuration to pass therethrough.

Preferably, and as shown in FIGS. 2 and 9, the two openings 15a, 15b are angularly offset relative to a transversal axis 12b of the shaft 12, to allow the two needles 55a, 55b, 155a, 155b to exit and to form an angle of about 15 to about 30 degree with respect to the transversal axis and to diverge as they pass through tissue (i.e., the two needles 55a, 55b, 155a, 155b are not parallel to the transversal axis 12b of the shaft 12, when the needles are in the operative or deployed position). The two openings 15a, 15b are also angularly offset relative to the longitudinal axis 12a of the shaft 12, to allow the two needles 55a, 55b, 155a, 155b to exit and to form an angle of about 10 to about 60 degrees, preferably of about 45 degrees, relative to the longitudinal axis 12a.

Figure 3:
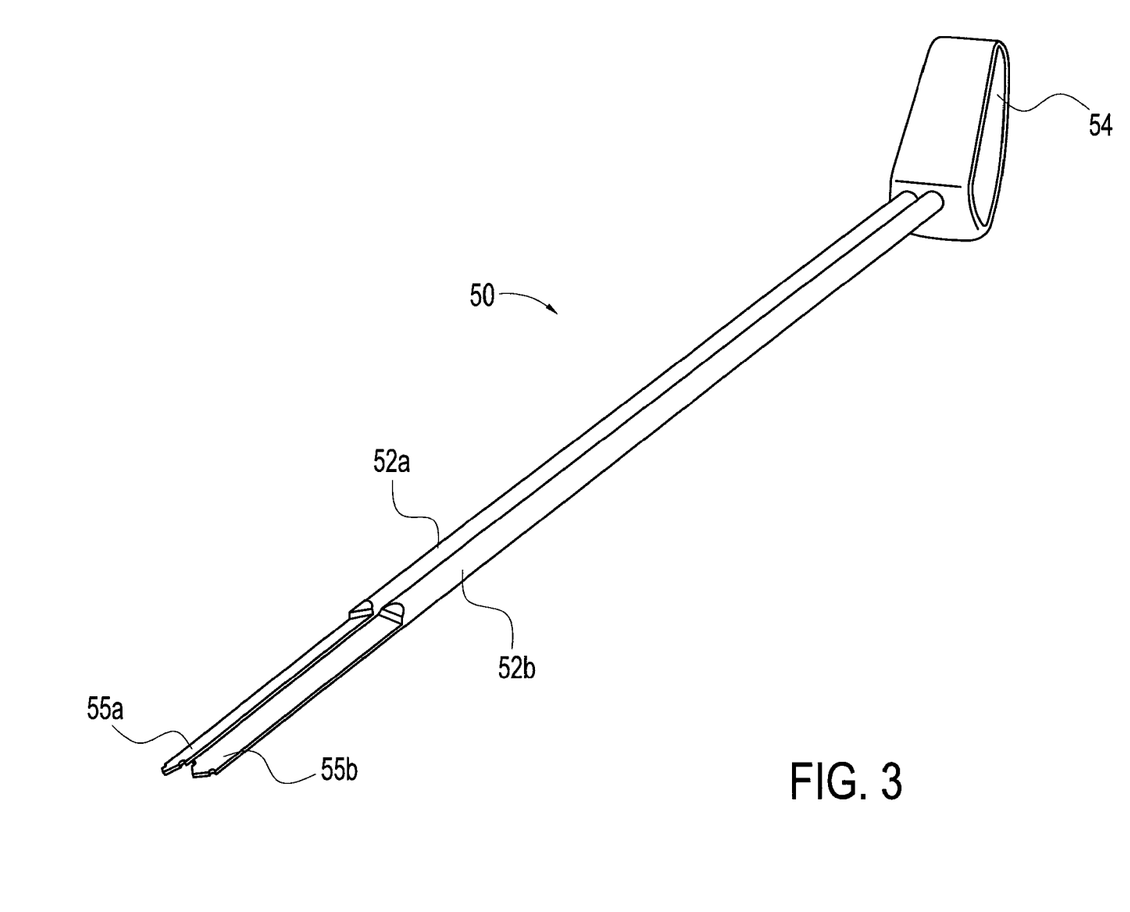
FIG. 3 is a perspective view of the dual-needle actuator of the suture passing instrument of FIG. 1, with the two needles undeployed.
Figure 4:
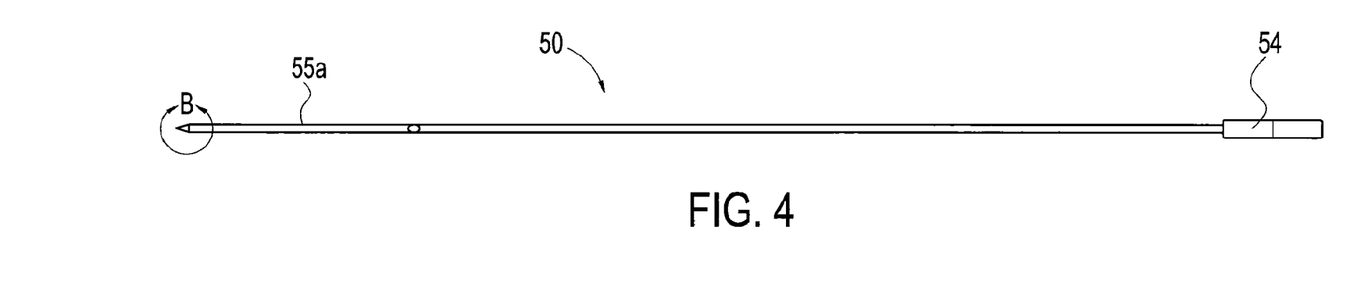
FIG. 4 illustrates a top view of the dual-needle actuator of FIG. 3.
Figure 5:
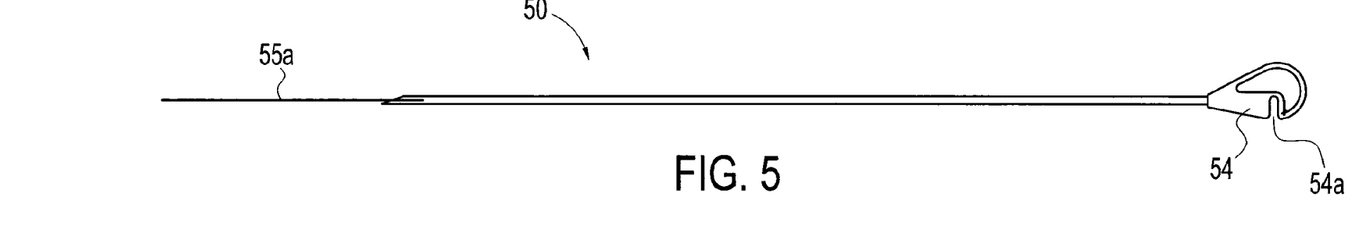
FIG. 5 illustrates a side view of the dual-needle actuator of FIG. 3.

FIG. 3 illustrates dual-needle actuator 50 comprising dual shafts 52a, 52b positioned in a side-by-side configuration and terminating in dual needles 55a, 55b, 155a, 155b. Shafts 52a, 52b are slidingly received in the axial throughbore (channel) of the elongated tubular member 12. Dual needles 55a, 55b, 155a, 155b are substantially disposed within the channel of the shaft 12 when the needles are in a non-operative, or non-piercing, position. In an operative position, the two needles are advanced distally to exit openings 15a, 15b in the lower jaw 10b. The needles may be bendable, so that they can be moved generally with an axial force and can be bent on a curve, for example 45 degrees, to move generally toward the upper jaw 10a. It is to be expressly understood that the needles can be bent at any angle and advanced in any direction.

Figure 6:
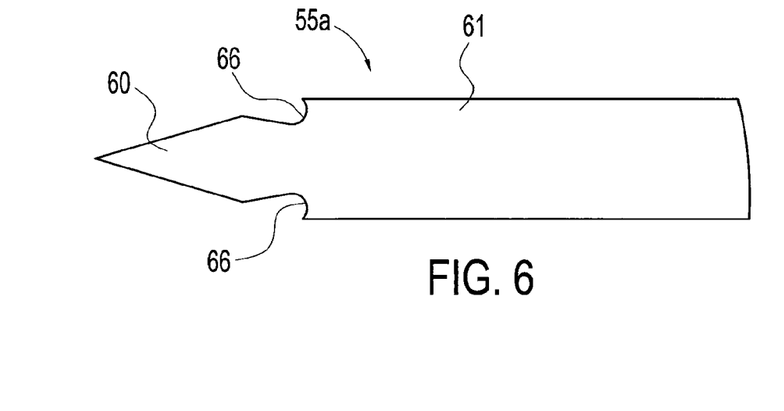
FIG. 6 illustrates an enlarged view of one of the two needles of the dual-needle actuator of FIG. 3.

As illustrated in FIGS. 2 and 6, each of the needles 55a, 55b has a pointed tip 60 at a distal end 61 of the needle and side barbs 66 provided from the pointed tip 60. The side barbs 66 are preferably about 2 mm from the pointed tip 60. The pointed tip 60 is designed to pierce the suture and the side barbs 66 are designed to carry the suture. Preferably, each of the needles 55a, 55b has a generally flat, narrow and elongate configuration. Needles 55a, 55b may preferably be formed of nitinol or other suitable material.

In an alternative embodiment illustrated in FIG. 9, needles 155a, 155b also have a flat, elongated configuration terminating in pointed tip 60 (similar to the embodiment of FIGS. 2 and 6). However, needles 155a, 155b are not provided with side barbs, but rather with a hook 166 that securely engages and captures the suture strand but without piercing it.

Dual-needle actuator 50 is provided within the shaft of the instrument and is designed to move the needles 55a, 55b, 155a, 155b in the lower jaw 10b, from a first position to a second position which is different from the first position. In the first position, the needles 55a, 55b, 155a, 155b may be about parallel to the longitudinal axis 12a of the instrument (in the undeployed position or non-operative), while in the second position, the needles 55a, 55b, 155a, 155b may form an angle of about 10 to about 60 degrees with the longitudinal axis 12a of the instrument (in the deployed or operative position). Preferably, needles 55a, 55b, 155a, 155b form an angle of about 45 degrees relative to the longitudinal axis 12a. Preferably, needles 55a, 55b, 155a, 155b form an angle of about 15 to about 30 degree relative to each other (as shown in FIG. 2, i.e., in a non-parallel orientation with the transversal axis 12b).

In use, the dual-needle actuator 50 is actuated relative to the longitudinal axis 12a of the tubular member, and needles 55a, 55b, 155a, 155b are pushed forward toward openings 15a, 15b to exit these openings as shown in FIGS. 2 and 9. Preferably, the dual needle shafts 52a, 52b are machined side by side at about 15 to 30 degree angle, to allow the two needle points to diverge as they pass through the tissue to be sutured (for example, a tendon).

Figure 7:
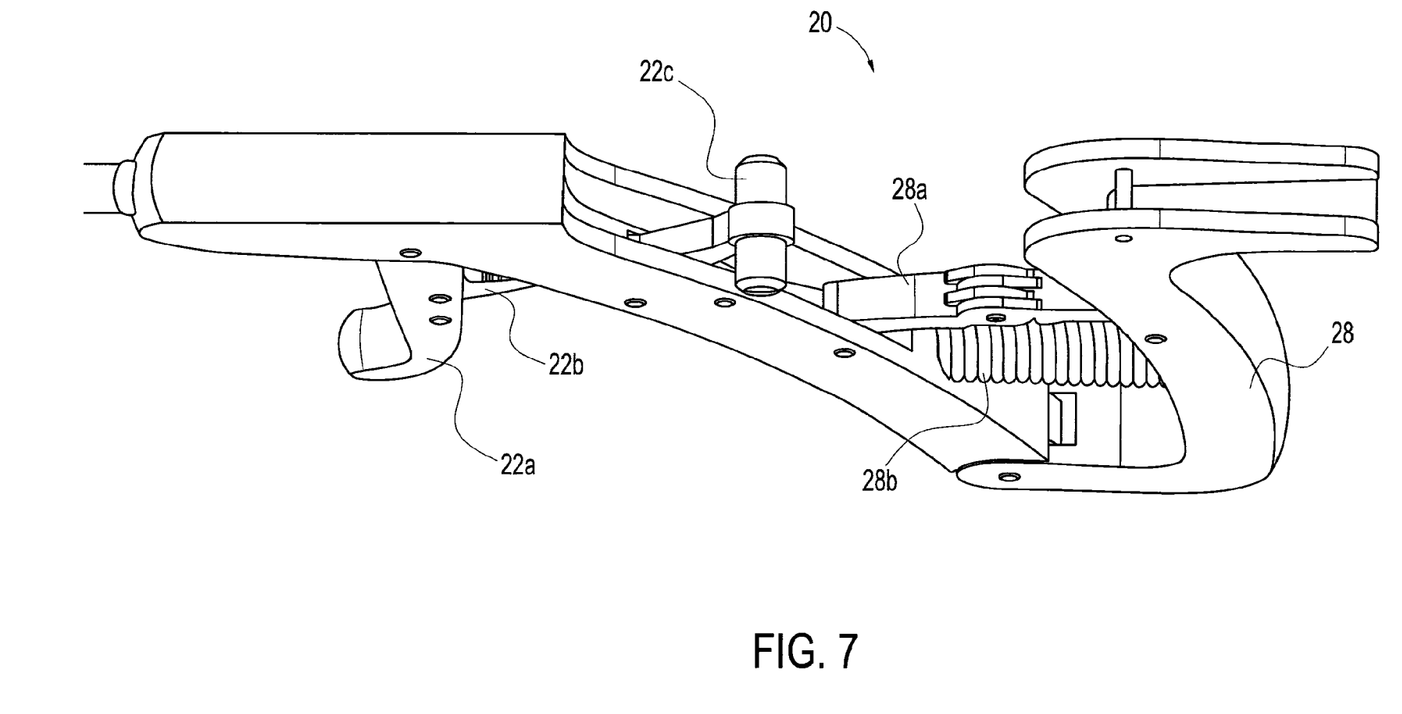
FIG. 7 illustrates a perspective view of the handle assembly of the suture passing instrument of FIG. 1.
Figure 8:
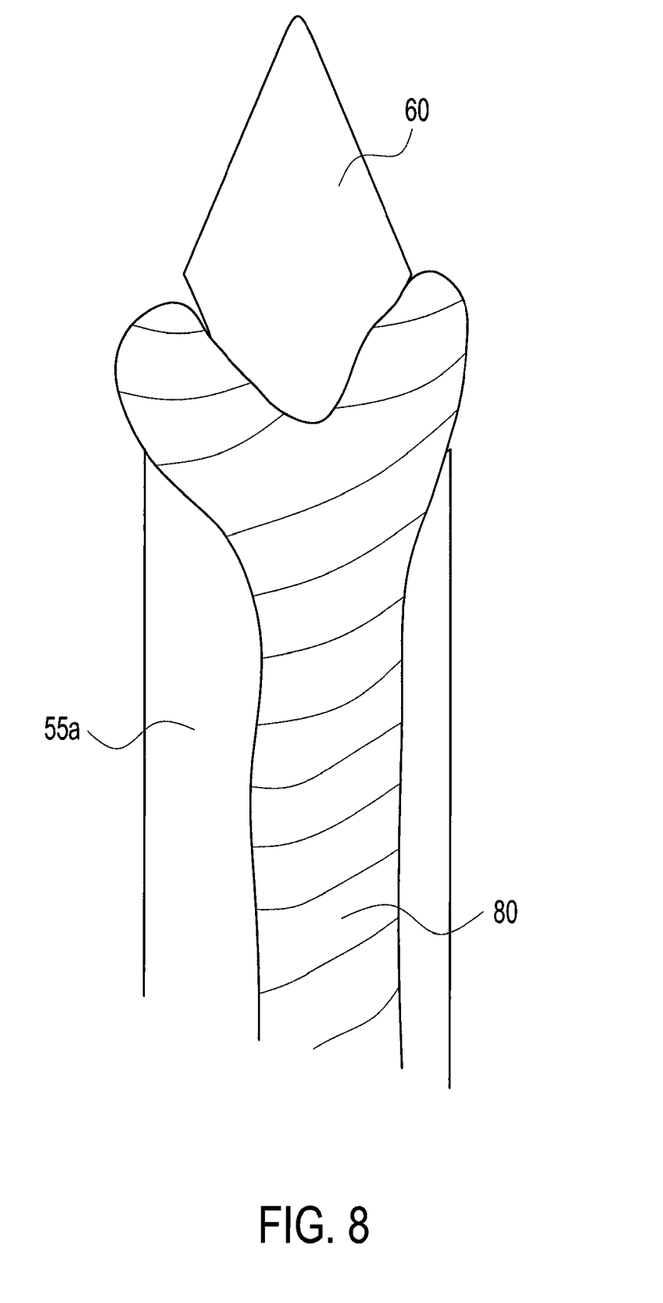
FIG. 8 illustrates an enlarged view of the needle of FIG. 6 with pierced suture.

Handle assembly 20 of the suturing instrument 100, 200, illustrated in FIGS. 1 and 7, is provided at the proximal end 11 of the instrument and includes a ratchet-like mechanism 22 and a handle 28, the ratchet-like mechanism 22 being pivotally connected to the handle 28. The ratchet-like mechanism 22 consists of a finger lever 22a with a ratchet 22b, and a releaser 22c with a hook 22d, the ratchet 22b and the hook 22d having a plurality of teeth to engage the finger lever 22a and the releaser 22c. The finger lever 22a and the releaser 22c perform substantially similar to a ratchet and a pawl. The finger lever 22a and the releaser 22c are pivotally connected to the distal end of the handle (not shown). The proximal and distal ends of the handle 28 (not shown) are linkably connected via a link 28a and tension between the proximal and distal ends may be additionally maintained using springs 28b (shown in FIG. 7 only).

The finger lever 22a is designed to move from a first position to a second position, with a spring 22a' provided to maintain tension on the finger lever 22a and to force the finger lever 22a to go back to a default position. At its default position, the finger lever 22a is farthest from the distal end of the handle 28.

The releaser 22c is designed to move from a first position to a second position, with a spring 22c' provided to maintain tension on the releaser 22c and to force the releaser 22c to go back to a default position. The releaser 22c further includes a portion designed to engage into a cross pin (not shown) and to securely hold the releaser 22c.

The suture passing instrument 100, 200 further includes an actuator 19, which is provided within the shaft 12 and at the distal end of the shaft. A proximal end of the actuator 19 is pivotally connected to the finger lever 22a and a distal end of the actuator 19 is pivotally connected to the upper jaw 10a. The actuator 19 is designed to move the upper jaw 10a from a first position to a second position as the finger lever 22a is moved from a first position to a second position. At the default position of the finger lever 22a, the upper jaw 10a is farthest from the lower jaw 10b.

With hand mechanism 20, a surgeon may seize and maintain tissue with jaws 10a, 10b. Using pusher 54 of dual-needle actuator 50, the two needles 55a, 55b, 155a, 155b are advanced to capture the suture strand positioned within securing mechanism 16, and to further carry and advance the captured suture strand through the tissue to be sutured.

A method of employing the suture passing instrument 100 of the present invention begins by loading the two needles 55a, 55b, 155a, 155b into the cannulation on the proximal end of the shaft 12 of the suture passing instrument 100, 200. The slot 54a (FIG. 5) on the proximal end of the dual-needle actuator 50 is engaged securely into a cross pin on the proximal end of handle 28 of the suture passing instrument. The needles facilitate passing the suture 80 (FIG. 8) through the tissue.

Suture 80 is loaded into the slots on the lower jaw 10b of the suture passing instrument 100, 200. By actuating the finger lever 22a on the suture passing instrument 100, 200, the upper jaw 10a and the lower jaw 10b are brought together (in a closed position), and the suture passing instrument 100 is advanced into the proximity of tissue to be sutured (for example, a joint such as the subacromial space). The two jaws may be held together (in the closed position) by actuating the releaser 22c (from an "Unlock" position to a "Lock" position). The upper jaw 10a is then disengaged from the lower jaw 10b by releasing the finger lever 22a and a desired bite of tissue is grasped.

With the jaws closed around the tissue (and preferably with the releaser 22c in the "Lock" position), the proximal and distal members of the handle 28 of the handle assembly 20 are squeezed together so that the two needles 55a, 55b, 155a, 155b are advanced distally, exiting the openings 15a, 15b on the lower jaw 10b. The pointed tips 60 of the needles 55a, 55b then pierce partly or completely through the suture 80 (FIG. 8) and the needles carry the suture. Alternatively, needles 155a, 155b do not pierce suture 80 but rather captures it in the two lateral slots or hooks 166 (FIG. 9). The needles and the suture are advanced distally using the handle assembly to advance the suture 80 through the tissue. The suture is captured and advanced by the two diverging needles 55a, 55b, 155a, 155b through the soft tissue. Finally, the suture 80 may be retrieved with a suture retriever or tissue grasper.

The suture passing instrument 100, 200 of the present invention, described above with reference to FIGS. 1-9, may be employed in various surgical medical procedures for advancing the suture in the proximity of a surgical site, and for employing the suture with a cannulated instrument during such surgical procedures. For example, the suture passing instrument may be employed in endoscopic procedures. Additionally, the suture passing instrument may be utilized in other general surgical and specialty procedures that require suturing at a remote site, such as inside the body. The suture passing instrument of the present invention may be also used in repairs where suture visibility or finger access can be limited.

It will be appreciated, of course, that while the suture passing instrument may be particularly useful for performing remote procedures through access sheaths, trocars and cannulated surgical instruments, it will also find use in open surgical procedures.

In an exemplary and illustrative embodiment only, a method of suturing tissue using the dual-needle suture passing instrument 100, 200 of the present invention comprises the steps of: (i) providing a dual-needle passing instrument 100 in the proximity of anatomical tissue to be sutured; (ii) positioning a flexible strand within a tip of the dual-needle passing instrument; (iii) engaging the suture with at least one of the two needles passing through the lower jaw of the instrument and exiting the lower jaw in a diverging orientation; and (iv) retrieving the suture.

According to another exemplary and illustrative embodiment only, a method of suturing a tissue using the dual-needle suture passing instrument 100, 200 of the present invention comprises the steps of: (i) loading two needles onto the instrument; (ii) loading a suture into the tip of the instrument; (iii) opening the jaws by releasing a finger lever and grasping the desired portion of tissue; (iv) closing the jaws using the finger lever and advancing the two needles (with suture engaged and captured thereon) through the tissue; (v) retracting the two needles; (vi) and retrieving the suture using a retriever or grasper.

Although the present invention has been described in connection with preferred embodiments, many modifications and variations will become apparent to those skilled in the art. While preferred embodiments of the invention have been described and illustrated above, it should be understood that these are exemplary of the invention and are not to be considered as limiting. Accordingly, it is not intended that the present invention be limited to the illustrated embodiments, but only by the appended claims.

What is claimed is:

1. A method of passing suture through tissue, the method comprising the steps of:
providing a suture passing instrument, the suture passing instrument comprising: a shaft having a longitudinal axis, a transversal axis orthogonal to the longitudinal axis, a distal end and a proximal end; a first jaw integral to the distal end of the shaft and configured to receive two side-by-side needles, the first jaw comprising two channels at its distal end to allow the needles to pass therethrough and a groove configured to retain a strand of suture thereon; a second jaw mounted to the distal end of the shaft and pivotally connected to the first jaw such that the second jaw is movable with respect to the first jaw; and a handle assembly comprising a handle;
loading two needles in the suture passing instrument by sliding the needles through a cannulation in the proximal end of the shaft such that a distal end of each of the needles is on the distal end of the shaft;
loading a suture onto the first jaw;
closing the second and first jaws and advancing the suture passing instrument in the vicinity of the tissue;
opening the second jaw and grasping a desired portion of the tissue by closing the second and first jaws with the tissue disposed between the jaws;
actuating the handle of the handle assembly to simultaneously advance the two needles, the needles passing through the two channels at the distal end of the shaft, the two channels extending from an upper surface of the first jaw to a lower surface of the first jaw, the two channels having respective openings on the upper surface of the first jaw, the two channels being angularly offset with respect to each other and with respect to the transversal axis of the shaft, such that the needles exit the openings at an angle with respect to each other and diverge as they exit, the needles capturing the suture and passing the captured suture through the tissue as they advance and diverge; and retracting the needles and retrieving the suture using a retriever or grasper.

2. The method of claim 1, wherein at least one of the two needles is a nitinol needle.

3. The method of claim 1, wherein the two needles have a similar configuration.

4. The method of claim 1, wherein the two needles have a different configuration.

5. The method of claim 1, wherein the step of advancing the needles and suture through the tissue further comprises:

advancing the needles by pushing proximal and distal members of the handle toward each other until the needles exit the openings on the first jaw and advance toward the second jaw;

capturing the suture with the needles; and advancing the needles and the captured suture simultaneously through the tissue.

6. The method of claim 1, wherein the suture is a braided suture comprising a plurality of high strength fibers.

7. The method of claim 1, wherein the needles form an angle of about 15 to 30 degrees with respect to the transversal axis of the instrument as they exit the two openings.

8. The method of claim 1, wherein the needles form an angle of about 45 degrees relative to the longitudinal axis of the instrument as they exit the two openings.

* * * * *